US00PP08419P

United States Patent [19]

Jessel, Jr.

[11] Patent Number: Plant 8,419

[45] Date of Patent: Oct. 12, 1993

[54] CARNATION PLANT NAMED CFPC CUPID

[75] Inventor: Walter H. Jessel, Jr., Salinas, Calif.

[73] Assignee: California Florida Plant Co., L.P., Salinas, Calif.

[21] Appl. No.: 930,837

[22] Filed: Aug. 13, 1992

[51] Int. Cl.[5] ..... A01H 5/00

[52] U.S. Cl. ..... Plt./70.6

[58] Field of Search ..... Plt./70.1, 70.2, 70.5, Plt./70.6, 70.7

*Primary Examiner*—Howard J. Locker

*Attorney, Agent, or Firm*—Christie, Parker & Hale

[57] ABSTRACT

A new carnation plant of low growth habit producing flowers of medium pink coloration.

1 Drawing Sheet

SUMMARY OF THE INVENTION

The present invention relates to a new and distinct variety of carnation plant which was originated by me in a controlled breeding program by my crossing as seed and pollen parents, two unnamed and unpatented seedlings of my creation. The varietal denomination of this new carnation is 'CFPC Cupid'.

Among the novel combination of characteristics possessed by the new variety which distinguishes it are dwarf plant growth habit, attractive medium pink flower coloring and suitability for growing as a pot plant in 4-inch pots.

'CFPC Cupid' was created in a breeding program to produce stable cultivars with dwarf plant growth habit that do not require use of growth retardants to achieve the dwarf plant growth and which are also suitable for growing as potted plants. It is presently believed that this dwarf growth habit is due to a homozygous recessive dwarfing gene.

The new variety will produce flower buds that open well under moderate light conditions such as may occur in the home. 'CFPC Cupid' may tolerate temperatures as high as 120° F. and as low as 10° to 16° F. and therefore has a wide temperature tolerance range.

If planted outdoor, 'CFPC Cupid' will continue to recycle growth and blooms and may be perennial in nature, depending upon climate.

Asexual reproduction by propagation by side shoot cuttings of the new variety as performed in Salinas, Calif., shows that the foregoing and other distinguishing characteristics come true to form and are established and transmitted through succeeding propagations. Although propagation by side shoot cuttings is described, other known methods of asexual reproduction may also be used to reproduce 'CFPC Cupid'.

BRIEF DESCRIPTION OF THE ILLUSTRATION

The accompanying illustration shows typical specimens of the vegetative growth and flowers of the new variety depicted in color as nearly true as it is reasonably possible to make the same in a color illustration of this character.

DESCRIPTION OF THE NEW VARIETY

The following is a detailed description of my new variety, with color terminology in accordance with The Royal Horticultural Society Colour Chart (R.H.S.C.C.). The terminology used in the color description herein refers to plate numbers in the aforementioned color chart. Color designations and color descriptions may deviate from the stated values depending upon varying environmental, seasonal and cultural conditions.

The new variety is one cultivar of a distinct type of true dwarf pot carnations, suitable for growing in 4" to 4½" pots (1 plant—1 pinch), and tolerant to temperatures of 10° F. to 120° F. No disease problems have been noted as yet. Keeping quality is generally 3 to 4 weeks. Flower buds will open from green buds to maturity with moderate light. 'CPFC Cupid' is distinct for its medium pink color, durability and the combination of aforementioned traits. If planted outdoors, CFPC Cupid will continue to recycle growth and blooms. For most sections of the country, CFPC Cupid appears to be perennial in nature.

The information provided herein is based on observations of plants grown inside commercial greenhouses at Salinas, Calif. The height of plant and flower and foliage size are established as an average using standard commercial cultural practices.

Name: 'CFPC Cupid'.

Classification:

*Botanical.*—*Dianthus caryophyllus.*

*Commercial.*—Dwarf carnation, pot forcing type.

Parentage:

*Female parent.*—Unnamed seedling, No. 880221.

*Male parent.*—Unnamed seedling, No. 880017.

Plant:

*Height.*—About 5½ to 6½ inches from base of plant after one pinching.

*Growing habit.*—Strong, semi-upright stems, free breaking.

*Blooming habit.*—As a spray.

*Blooming season.*—Year round.

*Rooting time.*—About 13 days.

*Mutation prone.*—Does not appear to be.

*Disease resistance.*—Good.

*Temperature tolerance.*—Wide range, 10° F.-16° F. to 120° F.

*Breaking action.*—Good.

Foliage:

*Color.*—Base: Near 142D. Upper side: Near 132A. Lower side: Near 131C.

*Size.*—About 3½ inches long, about ⅛ inch wide, thickness about 0.06 inch.

*Quantity.*—Numerous.

*Shape.*—Lanceolate.

*Texture.*—Smooth.

*Ribs.*—Central, keeled.
*Arrangement.*—Bi-lateral along stem.
*Stem color.*—Green.

Bud:
*Shape.*—Oval.
*Color.*—Green.
*Length.*—About ¾-inch.
*Diameter.*—About ½-inch.

Calyx:
*Number of sepals.*—About 6.
*Length.*—About ⅝-inch.
*Width.*—About ¼-inch.
*Color.*—Outside — near to 144A. Inside — Near to 145D. Base — near 145B.

Bloom:
*Shape.*—Round.
*Size.*—Diameter average: About 2-inches. Depth average: About 1-inch.
*Borne.*—As a spray; averages about 64 buds and flowers per potted plant (4-inch).
*Color.*—General tonality: Medium pink. Upper side: Near to 57A to 58B. Lower side: Near to 58C. Center: Near to 57A to 58B. Outer petals: Near to 62C.
*Keeping quality.*—About 3 weeks or more.
*Fragrance.*—Slight.

Petals:
*Number.*—About 47 to 49.
*Outer petals.*—Length: About 1½ inches. Width: About ¾-inch.
*Central petals.*—Length: About ¾-inch. Width: About ⅜-inch.
*Texture.*—Smooth.
*Form.*—Fan shaped.
*Appearance.*—Shiny.

Reproductive organs:
*Stamens.*—Number: About 17. Arrangement: Around the ovary.
*Anthers.*—Length: About ⅛-inch. Color: Near 159C.
*Filaments.*—Length: About 1-inch. Color: Near 155D.
*Pistil.*—Number: About 2. Color: Near to 155D to white. Length: About 1-inch.
*Stigma.*—Number: About 2. Color: Near 189A.
*Ovary.*—Shape: Conical. Color: Base — Green. Apex — Tan.
*Fertility.*—Appears to be fertile as male and female.

I claim:

1. A new and distinct variety of true dwarf pot carnation plant, substantially as shown and described.

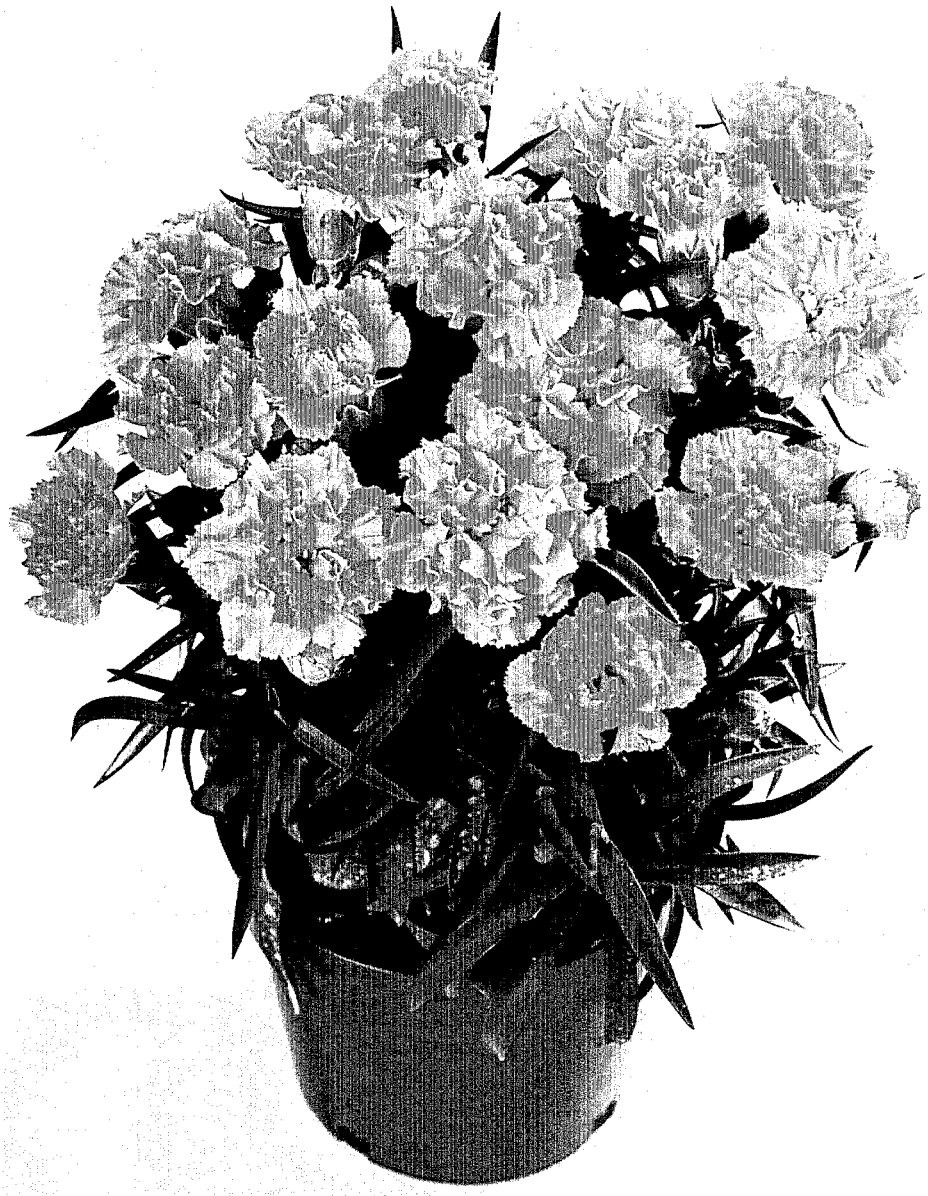

* * * * *